(12) United States Patent
Kawamuki (10) Patent No.: US 9,285,321 B2
(45) Date of Patent: Mar. 15, 2016

(54) FLUORESCENCE DETECTION DEVICE

(71) Applicant: Sharp Kabushiki Kaisha, Osaka-shi, Osaka (JP)

(72) Inventor: Ryohhei Kawamuki, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 14/438,255

(22) PCT Filed: Nov. 6, 2013

(86) PCT No.: PCT/JP2013/079960
§ 371 (c)(1),
(2) Date: Apr. 24, 2015

(87) PCT Pub. No.: WO2014/077158
PCT Pub. Date: May 22, 2014

(65) Prior Publication Data
US 2015/0276605 A1 Oct. 1, 2015

(30) Foreign Application Priority Data

Nov. 15, 2012 (JP) ................................. 2012-251086

(51) Int. Cl.
*G11B 7/09* (2006.01)
*G01N 21/64* (2006.01)
*G01N 27/447* (2006.01)

(52) U.S. Cl.
CPC ........ *G01N 21/6486* (2013.01); *G01N 21/6454* (2013.01); *G01N 21/6456* (2013.01); *G01N 27/44721* (2013.01); *G01N 27/44778* (2013.01); *G01N 2021/6463* (2013.01); *G01N 2201/061* (2013.01); *G01N 2201/10* (2013.01); *G01N 2201/103* (2013.01); *G01N 2201/105* (2013.01)

(58) Field of Classification Search
CPC ....................................................... G11B 7/09
See application file for complete search history.

(56) References Cited

U.S. PATENT DOCUMENTS

| 4,669,073 A * | 5/1987 | Wakabayashi | ........... G11B 7/08 250/201.5 |
| 2001/0046712 A1* | 11/2001 | Hang | ................. G01N 21/6452 436/172 |

FOREIGN PATENT DOCUMENTS

| JP | 10-003134 A | 1/1998 |
| JP | 2000-162126 A | 6/2000 |

* cited by examiner

*Primary Examiner* — Casey Bryant
(74) *Attorney, Agent, or Firm* — Keating & Bennett, LLP (57) ABSTRACT

A fluorescence detection device includes: a light source that emits excitation light in a first direction; a base unit (30) to which the light source is attached; an opening (30a) that is provided on a side in the first direction of the base unit (30) with respect to the light source; a cantilever (31) that is cantilevered to the base unit (30) to extend from an inner edge of the opening (30a) toward a center side of the opening (30a); an optical path conversion unit (20) that is fixed to a free end of the cantilever (31), converts a traveling direction of the excitation light emitted from the light source into a second direction different from the first direction, and irradiates a measurement object with the excitation light turned in the second direction; and a photodetection element that is disposed on a side of the opening (30a) opposite to the measurement object and detects fluorescence passing through the opening (30a) in fluorescence emitted from the measurement object irradiated with the excitation light. Accordingly, a loss in the fluorescence guided to the photodetection element can be reduced, and thus fluorescence detection efficiency can be improved.

12 Claims, 5 Drawing Sheets

FLUORESCENCE DETECTION DEVICE

TECHNICAL FIELD

The present invention relates to a fluorescence detection device, for example, a fluorescence detection device including an optical head that performs scanning at a high speed.

BACKGROUND ART

In the related art, fluorescence detection systems using fluorescent pigments as labeled substances have been widely used in the fields of biochemistry and molecular biology. The fluorescence detection systems can be used to perform, for example, gene arrangement, analysis of gene mutation and polymorphism, and evaluation of protein separation and identification and are thus used to develop drugs and the like.

As an evaluation method using fluorescent labeling, as described above, a method of distributing biological compounds such as proteins in gels through electrophoresis and acquiring the distributions of the biological compounds through fluorescence detection is well used. In the electrophoresis, an electric field gradient is generated in a solution such as a buffer solution by putting an electrode in the solution and causing a direct current to flow. At this time, when protein, Deoxyribonucleic acid (DNA), or ribonucleic acid (RNA) with a charge is present in the solution, molecules with a positive charge can be attracted to an anode and molecules with a negative charge can be attracted to a cathode. Thus, separation of the biological molecules can be performed.

Two-dimensional electrophoresis which is one of the evaluation methods using the foregoing electrophoresis is an evaluation method in which biomolecules are distributed in a gel two-dimensionally by combining two types of electrophoresis methods, and is considered to be the most effective method available to perform proteome analysis.

As a combination of the two types of electrophoresis methods, a combination of "isoelectric point electrophoresis using a difference in an isoelectric point of the individual protein" which is the first dimension and "sodium dodecylsulfate polyacrylamide gel electrophoresis (SDS-PAGE) performing separation with the molecular weight of the protein" which is the second dimension is generally used. Fluorescence pigments are added to proteins, which are biomolecules separated in this way, before electrophoresis is performed or after electrophoresis is performed.

Image reading devices that emit excitation light to a gel support in which biomolecules (proteins) are distributed two-dimensionally, the gel support being produced in the above manner, acquire generated fluorescence intensities, and display fluorescence distribution (protein distribution) images based on the fluorescence intensities are widely used in the fields of biochemistry and molecular biology.

As a method of maintaining a two-dimensional distribution of the biomolecules, a method of separating proteins in the gel and subsequently transferring the proteins from the gel to a membrane using electrophoresis or capillarity as well as maintaining the distribution of the biomolecules in the gel can be performed. In this case, as in the case of image reading performed using the gel support, the fluorescence distribution of a transfer support which is the membrane can be imaged by an image reading device.

As a first fluorescence detection device of the related art used in an image reading device that reads a biomolecule distribution image from a gel support or a transfer support in which the biomolecules are distributed two-dimensionally, as described above, there is an optical head scanning type device that includes an optical head that irradiates a sample with excitation light and that guides fluorescence generated from an excitation light emission unit to detection means and scanning means for moving the optical head over the sample at a constant speed (for example, see Japanese Unexamined Patent Application Publication No. 10-3134 (PTL 1)).

In the first fluorescence detection device of the related art, excitation light having a narrow beam emitted from a light source is reflected in a sample direction by a mirror, subsequently passes through a hole formed in a part of a mirror, and is collected at one point on the sample by a lens so that the sample is excited. At this time, the fluorescence generated from the sample follows the same optical path as the excitation light, is converted into parallel light by a lens, is subsequently reflected from a mirror surface with a hole, passes through a laser light cut filter, and is then detected.

In the first fluorescence detection device of the related art, among the fluorescence generated from the sample, a component of light that has passed through the hole is not guided to a photodetection element. However, since the emission angle of the fluorescence is wide, the diameter of the excitation beam becomes thick and most of the fluorescence emitted from the sample is guided to the photodetection element. The fluorescence intensity from each emission point is acquired by scanning the optical head over the sample two-dimensionally and a fluorescent image is generated based on the information regarding the fluorescence intensity.

As a second fluorescence detection device of the related art, there is a fluorescence detection device improving sensitivity more than the first fluorescence detection device described above (for example, see Japanese Unexamined Patent Application Publication No. 2000-162126 (PTL 2)). In the fluorescence detection device, a reflection optical system is disposed on a side of a sample opposite to a side on which an optical head is disposed in order to also detect fluorescence emitted from the opposite surface side, and thus the amount of fluorescence detected increases.

CITATION LIST

Patent Literature

PTL 1: Japanese Unexamined Patent Application Publication No. 10-3134
PTL 2: Japanese Unexamined Patent Application Publication No. 2000-162126

SUMMARY OF INVENTION

Technical Problem

However, when both of an excitation optical system and a detection optical system are mounted on a scanning module as in the first and second fluorescence detection devices of the related art, a part of the fluorescence is blocked, absorbed, or reflected by an optical element for branching between the excitation optical system and the detection optical system and the sensitivity of the photodetection element is lowered. Therefore, there is a problem that fluorescence detection efficiency deteriorates. Thus, the quality of an image read using the fluorescence detection device may deteriorate.

Accordingly, a task of the invention is to provide a fluorescence detection device capable of reducing a loss of fluorescence guided to a photodetection element, and thus improving fluorescence detection efficiency.

Solution to Problem

In order to resolve the foregoing problems, a fluorescence detection device according to the invention includes: a light source that emits excitation light in a first direction; a base unit to which the light source is attached; an opening that is provided on a side in the first direction of the base unit with respect to the light source; a cantilever that is cantilevered to the base unit to extend from an inner edge of the opening toward a center side of the opening; an optical path conversion unit that is fixed to a free end of the cantilever, converts a traveling direction of the excitation light emitted from the light source into a second direction different from the first direction, and irradiates a measurement object with the excitation light turned in the second direction; and a photodetection element that is disposed on a side of the opening (30a) opposite to the measurement object and detects fluorescence passing through the opening in fluorescence emitted from the measurement object irradiated with the excitation light.

In the fluorescence detection device according to an embodiment, a fixed end of the cantilever may be fixed on a side of the optical path conversion unit opposite to the light source and is fixed to the inner edge of the opening, and the cantilever may extend in the first direction from the free end to which the optical path conversion unit is fixed toward the fixed end.

In the fluorescence detection device according to an embodiment, the optical path conversion unit may have an adhesion surface in which an adhesive material is applied to a face provided on a side opposite to an incident side of the excitation light from the light source and facing in the first direction. The optical path conversion unit may be fixed to the cantilever by adhering the adhesion surface of the optical path conversion unit to the cantilever with the adhesive material.

In the fluorescence detection device according to an embodiment, the cantilever may have an installation surface on which the optical path conversion unit is installed. The optical path conversion unit may have a contact surface in planar contact with the installation surface of the cantilever, and the adhesion surface standing up relative to the installation surface of the cantilever. In a state in which the installation surface of the cantilever is in planar contact with the contact surface of the optical path conversion unit, a part of the cantilever may be adhered to the adhesion surface of the optical path conversion unit with the adhesive material so that the installation surface of the cantilever is not adhered to the contact surface of the optical path conversion unit.

In the fluorescence detection device according to an embodiment, the cantilever may have a wall portion with a shape protruding from the installation surface. The wall portion of the cantilever may have a wall surface facing the adhesion surface of the optical path conversion unit with a gap therebetween. The wall surface of the wall portion of the cantilever and the adhesion surface of the optical path conversion unit may be adhered with the adhesive material being filled therebetween.

In the fluorescence detection device according to an embodiment, the optical path conversion unit may be a light reflection member that has a triangular cross-sectional shape and converts an optical path through reflection. The light reflection member having the triangular cross-sectional shape may have the contact surface in planar contact with the installation surface of the cantilever, a reflection surface inclined with respect to an incident direction of the excitation light incident from the light source, and the adhesion surface standing up relative to the installation surface of the cantilever.

Advantageous Effects of Invention

As is apparent from the above description, according to the invention, even when a part of the fluorescence is blocked by the optical path conversion unit (optical element) changing the optical path of the excitation light, the optical path conversion unit is fixed to the cantilever so that the fluorescence blocked by the optical path conversion unit and the cantilever which is a support member of the optical path conversion unit is reduced. Therefore, an image with high quality can be obtained by increasing sensitivity. Accordingly, the loss of the fluorescence guided to the photodetection element can be reduced, and thus fluorescence detection efficiency can be improved.

DESCRIPTION OF EMBODIMENTS

Hereinafter, a fluorescence detection device of the invention will be described in detail with reference to the drawings according to an embodiment.

Figure 1:
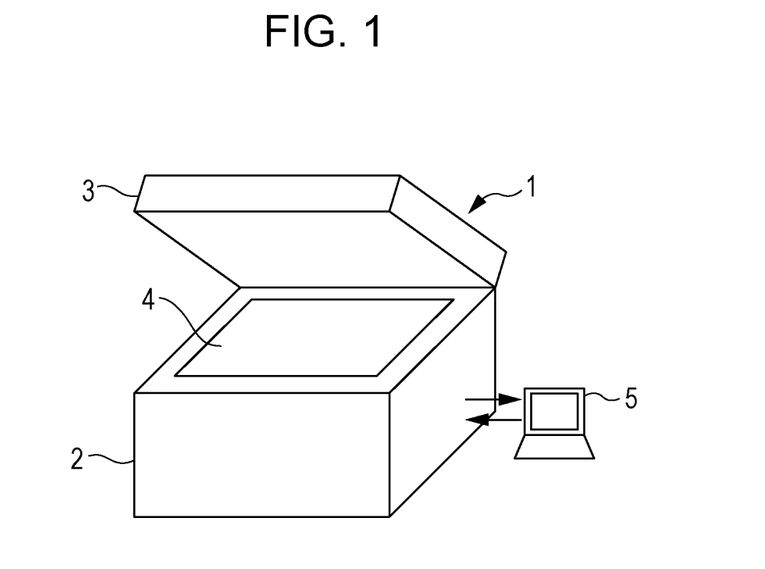
FIG. 1 is a diagram illustrating the outer appearance of a fluorescence detection device according to an embodiment of the invention.

FIG. 1 is a schematic diagram illustrating the fluorescence detection device according to an embodiment of the invention.

A fluorescence detection device 1 according to the embodiment includes a body 2 that forms a casing and a lid 3 that covers the upper surface of the body 2, as illustrated in FIG. 1. A sample table 4 formed of glass is provided on the upper surface of the body 2. For example, a gel support or a transfer support such as a membrane (none of which is illustrated) in which an organism-derived substance labeled with a fluorescent substance is distributed is set as a sample (measurement object) on the sample table 4.

An optical system is disposed on the lower side of the sample table 4. The sample set on the sample table 4 is irradiated from below with excitation light through the sample table 4 by a light irradiation optical system, and then fluorescence coming from the sample and passing through the sample table 4 is detected by the detection optical system. The detection optical system is connected to an external terminal such as a personal computer (PC) 5 and is subjected to measurement condition control or the like by the PC 5. The PC 5 generates a fluorescence image of the sample based on detected data and displays the generated fluorescence image or the like on a built-in display screen.

Figure 2:
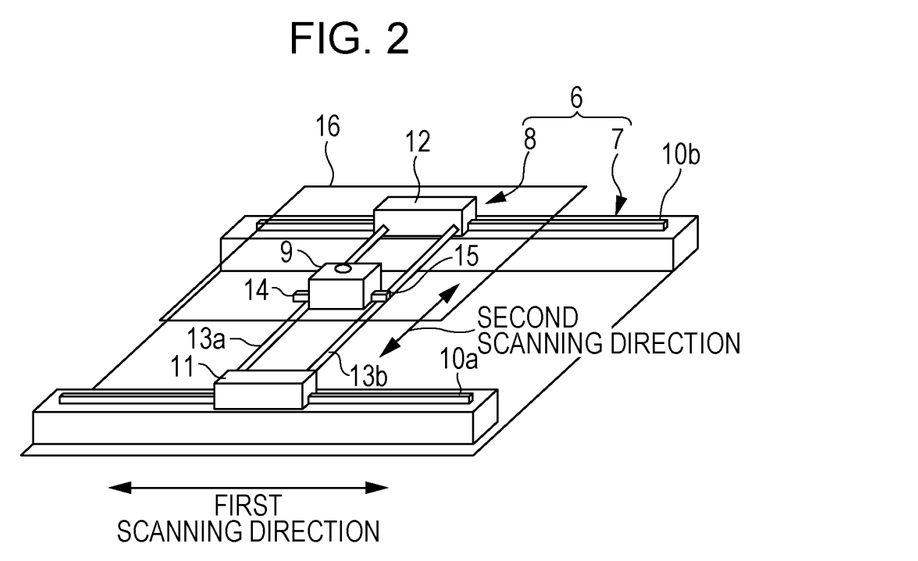
FIG. 2 is a diagram illustrating the outer appearance of a scanning stage installed below a sample table in FIG. 1.

FIG. 2 is a diagram illustrating the outer appearance of a scanning stage 6 installed below the sample table 4. As illustrated in FIG. 2, the scanning stage 6 is configured to include a first stage 7 serving as a reference and a second stage 8 mounted on the first stage 7. A scanning module 9 is mounted on the second stage 8. An excitation optical system irradiating the measurement object with the excitation light and the detection optical system detecting the fluorescence coming from the measurement object are stored in the scanning module 9. Thus, the excitation optical system and the detection optical system are integrated in the scanning module 9.

Two guide rails 10a and 10b that extend in a first scanning direction and face each other at a uniform interval are arranged in the first stage 7 included in the scanning stage 6. The second stage 8 includes a first guide member 11 that is guided by the guide rail 10a of the first stage 7 and reciprocates in the first scanning direction and a second guide member 12 that is guided by the guide rail 10b and reciprocates in the first scanning direction.

Two guide rails 13a and 13b that extend in a second scanning direction perpendicular to the first scanning direction and face each other at a uniform interval are installed between the first guide member 11 and the second guide member 12 included in the second stage 8. The scanning module 9 includes a first guide member 14 that is guided by the guide rail 13a and reciprocates in the second scanning direction and a second guide member 15 that is guided by the guide rail 13b and reciprocates in the second scanning direction.

According to a scanning method performed by the scanning stage 6 with the foregoing configuration, the first guide member 11 and the second guide member 12 of the second stage 8 are first guided by the guide rails 10a and 10b to be moved in the first scanning direction so that the second stage 8 is positioned with respect to the first stage 7. Subsequently, the first guide member 14 and the second guide member 15 of the scanning module 9 are guided by the guide rails 13a and 13b to be moved in the second scanning direction so that the scanning module 9 is positioned with respect to the second stage 8. Thereafter, the foregoing operations are repeated to two-dimensionally scan a sample 16 which is an example of the measurement object.

That is, in the embodiment, movement means in the first scanning direction is configured to include the guide rails 10a and 10b, the first guide member 11, and the second guide member 12 and movement means in the second scanning direction is configured to include the guide rails 13a and 13b, the first guide member 14, and the second guide member 15.

In a lower portion of the sample table 4 of the body 2 forming the casing, although detailed description is omitted, a driving unit formed by a motor, driving belts, ball screws, gears, a control board, a power source, wirings, and the like is installed below the scanning stage 6 in order to move the first guide member 11 and the second guide member 12 of the second stage 8 in the first scanning direction and in order to move the first guide member 14 and the second guide member 15 of the scanning module 9 in the second scanning direction.

Figure 3:
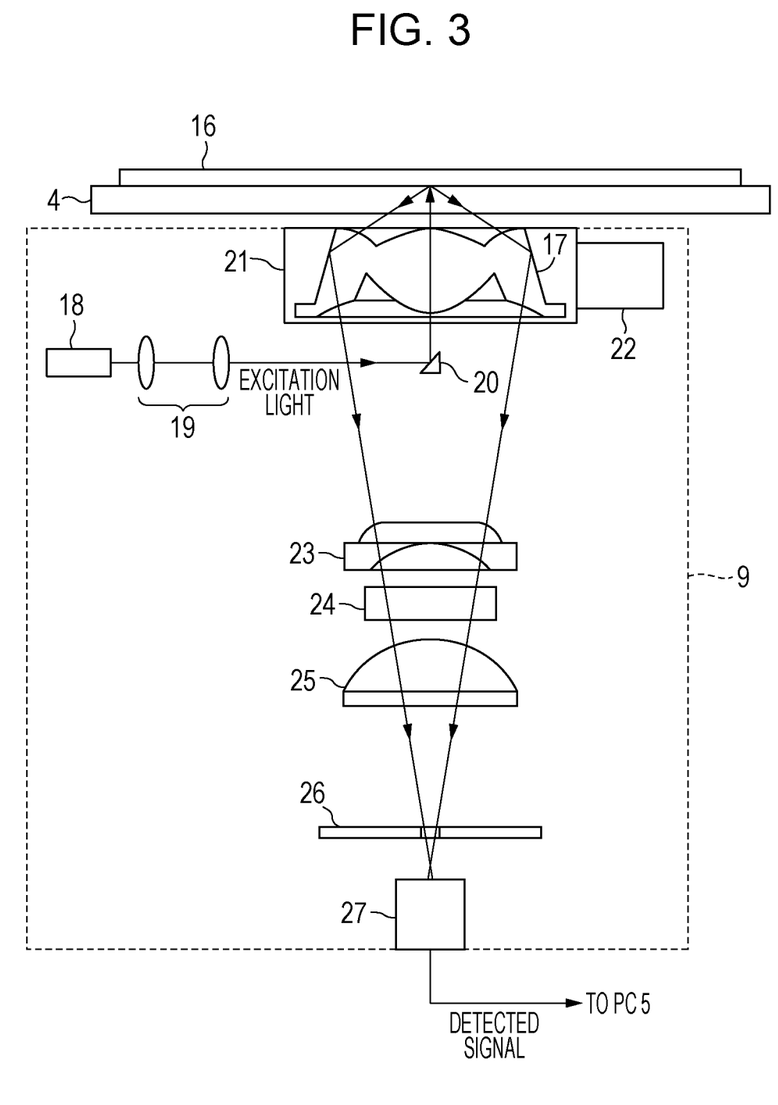
FIG. 3 is a longitudinal sectional view illustrating the basic configuration of a scanning module mounted on a second stage in FIG. 2.

FIG. 3 is a longitudinal sectional view illustrating the schematic configuration of the scanning module 9 mounted on the second stage 8 illustrated in FIG. 2. In FIG. 3, an objective lens 17 that is located near the sample table (glass) 4 and which collects the fluorescence from the sample 16 set on the sample table 4 is disposed in an upper portion inside the scanning module 9. A prism 20 which is an example of an optical path conversion unit that reflects the excitation light such as laser light emitted from the light source 18 and collected by a lens group 19 formed by a plurality of lenses so that the excitation light is incident on the objective lens 17 is disposed at a position at which the optical axis of the objective lens 17 is perpendicular to the optical axis of the excitation light of a light source 18.

The objective lens 17 is accommodated inside a lens holder 21. The lens holder 21 is configured to be movable in an optical axis direction of the objective lens 17 by a driving unit 22 such as a stepping motor. Thus, the objective lens 17 is configured to be movable in the optical axis direction along with the lens holder 21.

On the lower side of the prism 20 on the optical axis of the objective lens 17, a first lens 23 that converts the fluorescence coming from the sample 16 and collected by the objective lens 17 into parallel light, a wavelength filter 24 that reduces the amount of excitation light, a second lens 25 that collects the fluorescence passing through the wavelength filter 24, and a pinhole 26 that reduces the amount of stray light of the fluorescence passing through the second lens 25 are disposed in this order from the side of the prism 20. A detector 27 which is an example of a photodetection element detecting the fluorescence passing through the pinhole 26 is disposed on the lower side of the pinhole 26 on the optical axis of the objective lens 17.

In the scanning module 9 having the foregoing configuration, the excitation light emitted from the light source 18 is converged by the lens group 19, is subsequently reflected by the prism 20, passes through the objective lens 17 and the sample table 4, and is collected at one point on the lower surface of the sample 16. In this case, the length of the prism 20 in the longitudinal direction (which is a direction perpendicular to the optical axis of the lens group 19) of the prism 20 is short and the width of the prism 20 in the direction perpendicular to the longitudinal direction is narrow, and thus the excitation light from the light source 18 passes through only the neighborhood (an excitation light transmission portion) of the optical axis of the objective lens 17.

The fluorescence is emitted isotropically from a portion at which the sample 16 has been irradiated with the excitation light to the periphery. Then, a component of the emitted fluorescence which passes through the sample table 4 formed of glass and is incident on the objective lens 17 passes through the objective lens 17, the first lens 23, the wavelength filter 24, the second lens 25, and the pinhole 26 and is detected by the detector 27. A detected signal from the detector 27 is subjected to a process such as AD conversion by a built-in AD converter (not illustrated) or the like and is subsequently transmitted to the PC 5. In this way, a distribution of the fluorescence intensity at each measurement point on the sample 16 is recorded on an internal memory or the like.

Figure 4:
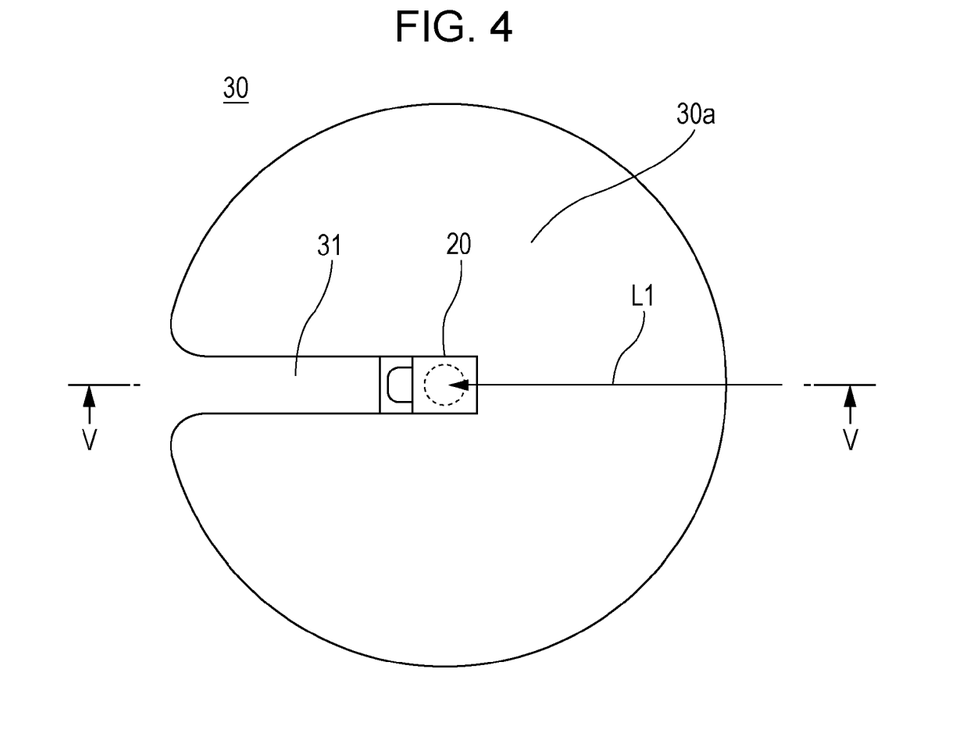
FIG. 4 is a plan view illustrating main units including a cantilever to which a prism is attached.

FIG. 4 is a plan view illustrating main units including a cantilever 31 to which the prism 20 is attached.

As illustrated in FIG. 4, the fluorescence detection device 1 includes a base unit 30 to which the light source 18 (illustrated in FIG. 3) emitting the excitation light (optical axis L1) in a first direction is attached, an opening 30a which has a substantially circular shape and is provided on the side of the base unit 30 in the first direction with respect to the light source 18, the cantilever 31 that is cantilevered in the base unit so as to extend from the inner edge of the opening 30a toward the center side of the opening 30a, and the prism 20 which is an optical path conversion unit and is fixed to the free end of the cantilever 31. In the embodiment, the opening 30a has a substantially circular shape, but the invention is not limited thereto. The opening 30a may have a shape through which an optical flux of the fluorescence collected by the objective lens 17 passes. The base unit 30 is a base member that supports each constituent of the scanning module 9.

The prism 20 converts a traveling direction of the excitation light emitted from the light source 18 into a second direction (which is perpendicular to the sheet surface of FIG. 4 and is an upper direction) different from the first direction, and thus the excitation light, the traveling direction of which has changed to the second direction, is emitted to the sample 16.

The fixed end of the cantilever 31 is fixed at the side opposite to the light source 18 emitting the excitation light to the prism 20 and is fixed to the inner edge of the opening 30a, and the cantilever 31 extends from the free end to which the prism 20 is fixed toward the fixed end in the first direction.

Figure 5:
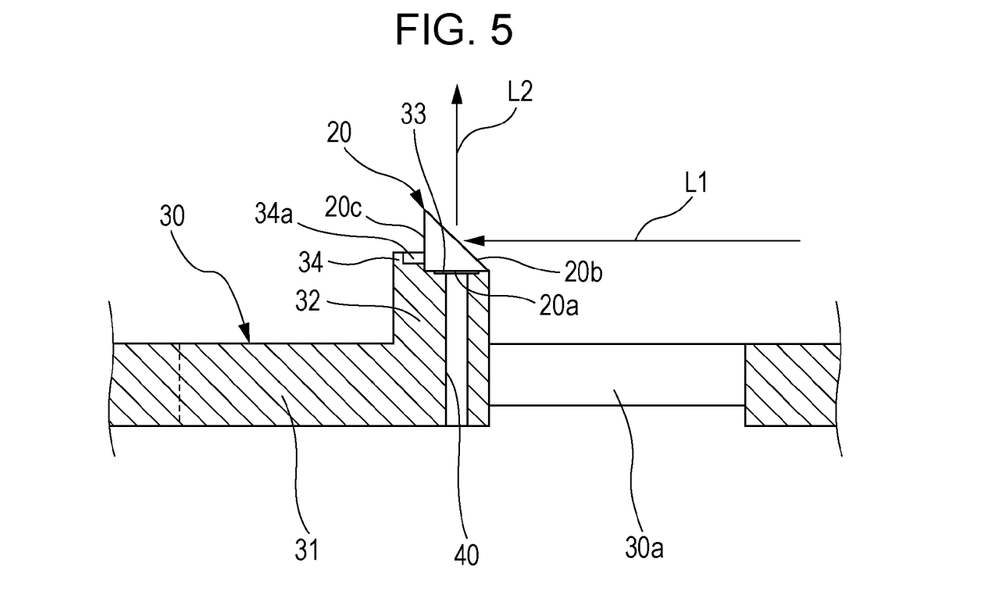
FIG. 5 is a sectional view taken along the line V-V of FIG. 4.
Figure 6:
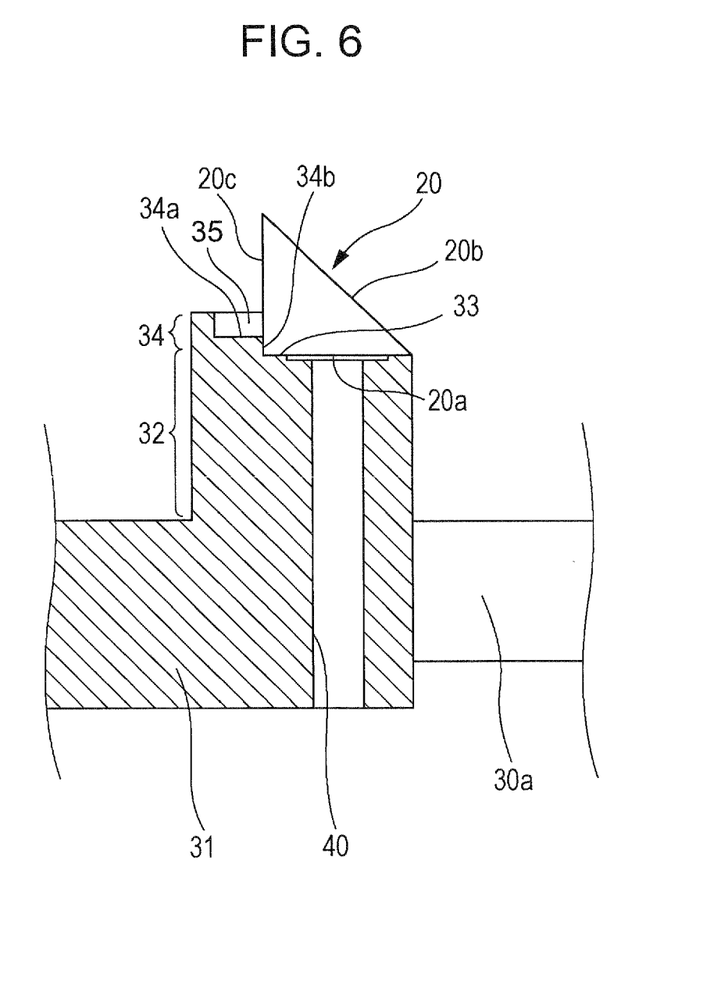
FIG. 6 is an enlarged view illustrating the main units of FIG. 5.

FIG. 5 is a sectional view taken along the line V-V of FIG. 4. FIG. 6 is an enlarged view illustrating the main units of FIG. 5. In FIG. 5, L1 indicates the optical axis of the excitation light emitted from the light source 18 disposed on the right side of the drawing and L2 indicates the optical axis of the excitation light after the excitation light has been reflected by the prism 20 and the optical path of the excitation light has been changed.

As illustrated in FIGS. 5 and 6, the cantilever 31 includes a bent portion 32 bent upward at the free end. An installation surface 33 on which the prism 20 is positioned is formed at the upper end of the bent portion 32 of the cantilever 31.

The prism 20 is a light reflection member that has a right-angled triangular shape in cross section and that converts the optical path through reflection. The prism 20 has a contact surface 20a which is in planar contact with the installation surface 33 of the cantilever 31, a reflection surface 20b which is a surface on which light from the light source 18 is incident and is a surface inclined with respect to an incident direction of the excitation light from the light source 18, and an adhesion surface 20c which is a surface opposite to the side on which the excitation light from the light source 18 is incident and stands up forming a substantially right angle with the installation surface 33 of the cantilever 31.

On the adhesion surface 20c of the prism 20, an adhesive material is applied to a face provided on a side opposite to an incident side of the excitation light from the light source 18 facing in the first direction. The prism 20 is fixed to the cantilever 31 by adhering the adhesion surface 20c of the prism 20 to the cantilever 31 with the adhesive material.

In the cantilever 31, a wall portion 34 with a shape protruding from the installation surface 33 is formed in an upper portion of the bent portion 32. A concave portion 35 in which the side of the prism 20 is opened is formed on the wall portion 34. The wall portion 34 has a wall surface 34a facing the adhesion surface 20c of the prism 20 with a gap therebetween. The concave portion 35 between the wall surface 34a of the wall portion 34 of the cantilever 31 and the adhesion surface 20c of the prism 20 is filled with an adhesive material.

As illustrated in FIGS. 5 and 6, a vacuum chuck through hole 40 extending downward from the substantially central portion of the installation surface 33 of the cantilever 31 is formed. By applying and adhering the adhesive material to the adhesion surface 20c when the contact portion between the prism 20 and the cantilever 31 come into close contact through vacuum adsorption using the through hole 40, it is possible to further improve positioning accuracy.

Here, a second wall surface 34b which is substantially perpendicular to the installation surface 33 is formed on the wall portion 34 formed in the upper portion of the bent portion 32 of the cantilever 31. The second wall surface 34b is at right angles to the excitation light emitted from the light source 18 (illustrated in FIG. 3) in the first direction. Thus, a corner in which the adhesion surface 20c is at right angles to the contact surface 20a of the prism 20 having the right-angled triangular shape in cross section is fitted into a portion in which the installation surface 33 is at right angles to the second wall surface 34b, so that the prism 20 is positioned in the first direction. That is, the prism 20 is positioned in the first direction and the orientation of the reflection surface 20b of the prism 20 is set so that a straight line perpendicular to the reflection surface 20b of the prism 20 lies on the same plane as the optical axis L1 of the excitation light from the light source 18 and the optical axis L2 of the excitation light.

Figure 7:
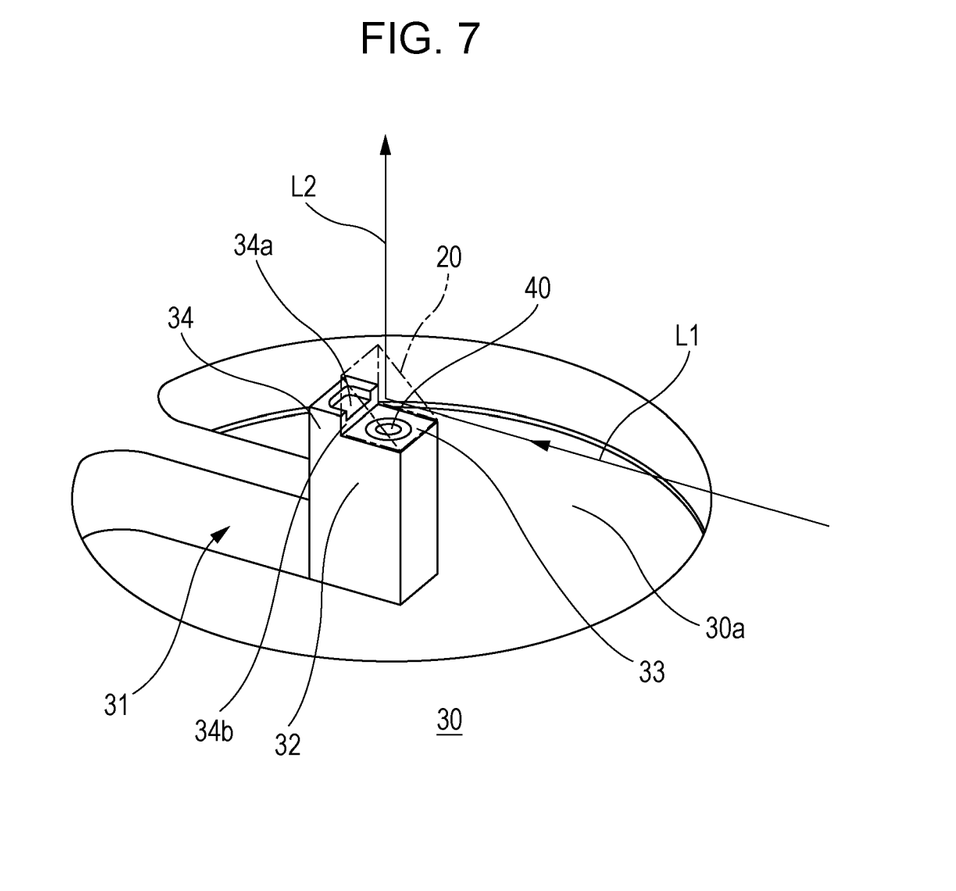
FIG. 7 is a perspective view illustrating the main units including the cantilever to which the prism is attached when viewed from the upper side.

FIG. 7 is a perspective view illustrating the main units including the cantilever 31 to which the prism 20 is attached when viewed from the upper side. As illustrated in FIG. 7, the concave portion 35 filled with the adhesive material is located on the upper side from the second wall surface 34b and is adhered to the upper side from the lower end of the adhesion surface 20c of the prism 20. Therefore, the cantilever 31 and the prism 20 can be stably adhered to each other and the positioning accuracy can be prevented from deteriorating since the adhesive material is sandwiched between the installation surface 33 of the cantilever 31 and the contact surface 20a of the prism 20.

In the fluorescence detection device with the foregoing configuration, the traveling direction of the excitation light emitted in the first direction from the light source 18 fixed to the base unit 30 is converted into the second direction different from the first direction by the prism 20 and the excitation light, the traveling direction of which is changed to the second direction, is emitted to the sample 16 which is the measurement object. The prism 20 is cantilevered to the base unit so as to extend from the inner edge of the opening 30a of the base unit 30 formed in the first direction with respect to the light source 18 toward the center side of the opening 30a. The fluorescence coming from the sample 16 irradiated with the excitation light from the light source 18 via the prism 20 passes through the opening 30a via the objective lens 17. Of the fluorescence coming from the sample 16 irradiated with the excitation light, the fluorescence passing through the opening 30a is detected by the detector 27 which is a photo-detection element disposed opposite the sample 16 with the opening 30a therebetween. Thus, the fluorescence emitted from the sample 16 passes through the entire portion except for the cantilever 31 in at least the opening 30a which is a periphery portion centered on the prism 20 by using the cantilever 31 for the fixing of the prism 20. Therefore, the aperture ratio in the optical path of the fluorescence can be improved. Accordingly, a loss in the fluorescence guided to the detector 27 can be reduced, and thus fluorescence detection efficiency can be improved. By integrating the excitation optical system and the detection optical system, the optical path of the fluorescence can be shortened and weak fluorescence can be detected without loss. Therefore, an image with high sensitivity can be obtained.

The extension direction of the cantilever 31 is opposite to the light incident side (the side of the light source 18) and the cantilever 31 is not present on the incident side of the fluorescence from the prism 20. Therefore, the optical path is not inhibited because a part of the incident fluorescence arrives at the cantilever 31.

Since the adhesion surface 20c to which the adhesive material is applied is formed on the side opposite to the side on which the light from the light source 18 of the prism 20 is incident, the excitation light is not emitted to, for example, a surface opposite the reflection surface 20b converting the optical path of the excitation light. Therefore, the optical path of the excitation light is not disturbed because the light is emitted to the portion to which the adhesive material has been applied.

The contact surface 20a of the prism 20 in planar contact with the installation surface 33 of the cantilever 31 can be used for positioning with high accuracy and the adhesive material is not applied to this portion. Therefore, positioning accuracy can be prevented from deteriorating due to the adhesive material being inserted between contact portions of the mutual planar surfaces and the planar surfaces not completely coming into close contact with each other. That is, the planar surface of the contact surface 20a of the prism 20 is completely in contact with the planar surface of the installation surface 33 of the cantilever 31, and thus the positioning can be performed with high accuracy. On the other hand, the adhesion surface 20c to which the adhesive material is applied and that is on the side of the prism 20 opposite to that on which the light from the light source 18 is incident is adhered to the cantilever 31 with the adhesive material. Thus, by separating the uses of the contact surface 20a for the positioning of the prism 20 and the adhesion surface 20c for the adhering of the prism 20 from each other, reliable adhering can be performed while positioning accuracy is maintained.

By providing a portion between the wall surface of the wall portion of the cantilever 31 and the adhesion surface 20c of the prism 20 to be filled with the adhesive material, the prism 20 and the cantilever 31 can be adhered more strongly at the time of adhering with the adhesive material.

The prism 20 is a light reflection member that has the triangular cross-sectional shape and that converts the optical path through reflection, and is a so-called reflective prism. The surfaces of the optical reflection member function as the contact surface 20a, the adhesion surface 20c, and the reflection surface 20b. Therefore, the optical path conversion unit can be realized with a simple prism structure.

In the foregoing embodiment, the cantilever is disposed in the direction opposite to the direction in which the excitation light is incident on the optical path conversion unit (optical element) and the cantilever is provided with means (for example, a positioning unit that presses the optical path conversion unit or a portion adhering the optical path conversion unit) for fixing the optical path conversion unit. Thus, an area blocking the fluorescence does not increase and the excitation light is not blocked by the positioning unit or the adhering portion.

In the foregoing embodiment, the fluorescence detection device 1 using the prism 20 as the optical path conversion unit has been described, but the optical path conversion unit is not limited. The invention may be applied to a fluorescence detection device that includes a light reflection member such as a mirror converting the traveling direction of the excitation light emitted in the first direction from the light source in the second direction different from the first direction.

In the foregoing embodiment, the optical axis L1 of the excitation light emitted from the light source 18 in the first direction is perpendicular to the optical axis L2 in the second direction in which the optical path is converted by the prism 20, but the invention is not limited to the second direction perpendicular to the first direction. The second direction with respect to the first direction may be appropriately set according to, for example, the disposition of the measurement object, the light source, the base unit, the optical path conversion unit, and the photodetection element.

The specific embodiment of the invention has been described, but the invention is not limited to the foregoing embodiment and can be modified in various ways within the scope of the invention.

The fluorescence detection device according to the invention includes: the light source 18 that emits excitation light in the first direction; the base unit 30 to which the light source 18 is attached; the opening 30a that is provided on the side in the first direction of the base unit 30 with respect to the light source 18; the cantilever 31 that is cantilevered to the base unit 30 to extend from the inner edge of the opening 30a toward the center side of the opening 30a; the optical path conversion unit 20 that is fixed to the free end of the cantilever 31, converts the traveling direction of the excitation light emitted from the light source 18 into the second direction different from the first direction, and irradiates a measurement object with the excitation light turned in the second direction; and the photodetection element 27 that is disposed on the side of the opening 30a opposite to the measurement object 16 and detects fluorescence passing through the opening 30a in fluorescence emitted from the measurement object 16 irradiated with the excitation light.

In the foregoing configuration, the optical path conversion unit 20 converts the traveling direction of the excitation light emitted in the first direction from the light source 18 fixed to the base unit 30 into the second direction different from the first direction and irradiates the measurement object 16 with the excitation light, the traveling direction of which is changed to the second direction. The optical path conversion unit 20 is cantilevered to the base unit 30 so as to extend from the inner edge of the opening 30a provided on the side in the first direction of the base unit with respect to the light source 18 toward the center side of the opening 30a. The fluorescence emitted from the measurement object 16 to which the excitation light is irradiated from the light source 18 via the optical path conversion unit 20 passes through the opening 30a. The fluorescence passing through the opening 30a in the fluorescence emitted from the measurement object 16 irradiated with the excitation light is detected by the photodetection element 27 that is disposed on the opposite side to the measurement object 16 with respect to the opening 30a. Thus, the fluorescence emitted from the measurement object 16 passes through at least the entire portion except for the cantilever 31 in at least the opening 30a that is a periphery portion centered on the optical path conversion unit 20 by using the cantilever 31 for the fixing of the optical path conversion unit 20. Therefore, an aperture ratio in the optical path of the fluorescence can be improved. Accordingly, a loss in the fluorescence guided to the photodetection element 27 can be reduced, and thus fluorescence detection efficiency can be improved. By integrating the excitation optical system and the detection optical system, the optical path of the fluorescence can be shortened and weak fluorescence can be detected without loss. Therefore, an image with high sensitivity can be obtained.

In the fluorescence detection device according to an embodiment, a fixed end of the cantilever 31 is fixed on a side of the optical path conversion unit 20 opposite to the light source 18 and is fixed to the inner edge of the opening 30a, and the cantilever 31 extends in the first direction from the free end to which the optical path conversion unit 20 is fixed toward the fixed end.

According to the foregoing embodiment, the extension direction of the cantilever 31 is opposite to the light incident side and the cantilever 31 is not present on the incident side of the fluorescence from the optical path conversion unit 20. Therefore, the optical path through which a part of the incident fluorescence arrives at the cantilever 31 is not inhibited.

In the fluorescence detection device according to an embodiment, the optical path conversion unit 20 has an adhesion surface 20c in which an adhesive material is applied to a face provided on a side opposite to an incident side of the excitation light from the light source 18 and facing in the first direction. The optical path conversion unit 20 is fixed to the cantilever 31 by adhering the adhesion surface 20c of the optical path conversion unit 20 to the cantilever 31 with the adhesive material.

According to the foregoing embodiment, since the adhesion surface 20c to which the adhesive material is applied is formed on the opposite side to the side on which the light from the light source 18 of the optical path conversion unit 20 is incident, the excitation light is not emitted to a surface opposite the reflection surface 20b converting the optical path of the excitation light. Therefore, the optical path of the excitation light is not disturbed because the light is emitted to the portion to which the adhesive material is applied.

In the fluorescence detection device according to an embodiment, the cantilever 31 has an installation surface 33 on which the optical path conversion unit 20 is installed. The optical path conversion unit 20 has a contact surface 20a in planar contact with the installation surface 33 of the cantilever 31, and the adhesion surface 20c standing up relative to the installation surface 33 of the cantilever 31. In a state in which the installation surface 33 of the cantilever 31 is in planar contact with the contact surface 20a of the optical path conversion unit 20, a part of the cantilever 31 is adhered to the adhesion surface 20c of the optical path conversion unit 20 with the adhesive material so that the installation surface 33 of the cantilever 31 is not adhered to the contact surface 20a of the optical path conversion unit 20.

According to the foregoing embodiment, the contact surface 20a of the optical path conversion unit 20 in planar contact with the installation surface 33 of the cantilever 31 can be used for positioning with high accuracy and the adhesive material is not applied to this portion. Therefore, positioning accuracy can be prevented from deteriorating due to the adhesive material being inserted between contact portions of the mutual planar surfaces and the planar surfaces not completely coming into close contact with each other. That is, the planar surface of the contact surface 20a of the optical path conversion unit 20 is completely in contact with the planar surface of the installation surface 33 of the cantilever 31, and thus the positioning can be performed with high accuracy. On the other hand, the adhesion surface 20c to which the adhesive material is applied and that is on the side of the optical path conversion unit 20 opposite to that on which the light from the light source 18 is incident is adhered to the cantilever 31 with the adhesive material. Thus, by separating the uses of the contact surface 20a for the positioning of the optical path conversion unit 20 and the adhesion surface 20c for the adhering of the optical path conversion unit 20 from each other, reliable adhering can be performed while positioning accuracy is maintained.

In the fluorescence detection device according to an embodiment, the cantilever 31 has a wall portion with a shape protruding from the installation surface 33. The wall portion of the cantilever 31 has a wall surface facing the adhesion surface 20c of the optical path conversion unit 20 with a gap therebetween. The wall surface of the wall portion of the cantilever 31 and the adhesion surface 20c of the optical path conversion unit 20 are adhered with the adhesive material being filled therebetween.

According to the foregoing embodiment, by providing a portion between the wall surface of the wall portion of the cantilever 31 and the adhesion surface 20c of the optical path conversion unit 20 to be filled with the adhesive material, the optical path conversion unit 20 and the cantilever 31 can be adhered more strongly at the time of the adhering with the adhesive material.

In the fluorescence detection device according to an embodiment, the optical path conversion unit 20 is a light reflection member that has a triangular cross-sectional shape and converts an optical path through reflection. The light reflection member having the triangular cross-sectional shape has the contact surface 20a in planar contact with the installation surface 33 of the cantilever 31, a reflection surface 20b inclined with respect to an incident direction of the excitation light incident from the light source 18, and the adhesion surface 20c standing up relative to the installation surface 33 of the cantilever 31.

According to the foregoing embodiment, the optical path conversion unit 20 is a light reflection member having the triangular cross-sectional shape and converting the optical path through reflection and is a so-called reflective prism. The surfaces of the optical reflection member function as the contact surface 20a, the adhesion surface 20c, and the reflection surface 20b. Therefore, the optical path conversion unit 20 can be realized with a simple prism structure.

REFERENCE SIGNS LIST

1 FLUORESCENCE DETECTION DEVICE
2 BODY
3 LID
4 SAMPLE TABLE
5 PC
6 SCANNING STAGE
7 FIRST STAGE
8 SECOND STAGE
9 SCANNING MODULE
10a, 10b GUIDE RAILS
11 FIRST GUIDE MEMBER
12 SECOND GUIDE MEMBER
13a, 13b GUIDE RAILS
14 FIRST GUIDE MEMBER
15 SECOND GUIDE MEMBER
16 MEASUREMENT OBJECT (SAMPLE)
17 OBJECTIVE LENS
18 LIGHT SOURCE
19 LENS GROUP
20 PRISM (OPTICAL PATH CONVERSION UNIT)
20a CONTACT SURFACE
20b REFLECTION SURFACE
20c ADHESION SURFACE
21 LENS HOLDER
22 DRIVING UNIT
23 FIRST LENS
24 WAVELENGTH FILTER
25 SECOND LENS
26 PINHOLE
27 DETECTOR (PHOTODETECTION ELEMENT)
30 BASE UNIT
30a OPENING
31 CANTILEVER
32 BENT PORTION
33 INSTALLATION SURFACE
34 WALL PORTION
34a WALL SURFACE
34b WALL SURFACE
35 CONCAVE PORTION
40 THROUGH HOLE

The invention claimed is:
1. A fluorescence detection device comprising:
a light source that emits excitation light in a first direction;
a base unit to which the light source is attached;
an opening that is defined in a side of the base unit, the side of the base unit extending in the first direction;
a cantilever that is cantilevered to the base unit to extend from an edge of the base unit that defines the opening and toward a center of the opening;
an optical path conversion unit that is fixed to a free end of the cantilever, converts a traveling direction of the excitation light emitted from the light source into a second direction different from the first direction, and irradiates a measurement object with the excitation light turned in the second direction; and a photodetection element that is disposed on a side of the opening opposite to the measurement object and detects fluorescence passing through the opening in fluorescence emitted from the measurement object irradiated with the excitation light.

2. The fluorescence detection device according to claim 1, wherein a fixed end of the cantilever is fixed on a side of the optical path conversion unit opposite to the light source and is fixed to the inner edge of the opening, and the cantilever extends in the first direction from the free end to which the optical path conversion unit is fixed toward the fixed end.

3. The fluorescence detection device according to claim 1,
wherein the optical path conversion unit has an adhesion surface in which an adhesive material is applied to a face provided on a side opposite to an incident side of the excitation light from the light source and facing in the first direction, and
wherein the optical path conversion unit is fixed to the cantilever by adhering the adhesion surface of the optical path conversion unit to the cantilever with the adhesive material.

4. The fluorescence detection device according to claim 3,
wherein the cantilever has an installation surface on which the optical path conversion unit is installed,
wherein the optical path conversion unit has a contact surface in planar contact with the installation surface of the cantilever, and the adhesion surface standing up relative to the installation surface of the cantilever, and
wherein, in a state in which the installation surface of the cantilever is in planar contact with the contact surface of the optical path conversion unit, a part of the cantilever is adhered to the adhesion surface of the optical path conversion unit with the adhesive material so that the installation surface of the cantilever is not adhered to the contact surface of the optical path conversion unit.

5. The fluorescence detection device according to claim 4,
wherein the cantilever has a wall portion with a shape protruding from the installation surface,
wherein the wall portion of the cantilever has a wall surface facing the adhesion surface of the optical path conversion unit with a gap therebetween, and
wherein the wall surface of the wall portion of the cantilever and the adhesion surface of the optical path conversion unit are adhered with the adhesive material being filled therebetween.

6. The fluorescence detection device according to claim 4,
wherein the optical path conversion unit is a light reflection member that has a triangular cross-sectional shape and converts an optical path through reflection, and
wherein the light reflection member having the triangular cross-sectional shape has the contact surface in planar contact with the installation surface of the cantilever, a reflection surface inclined with respect to an incident direction of the excitation light incident from the light source, and the adhesion surface standing up relative to the installation surface of the cantilever.

7. The fluorescence detection device according to claim 1, wherein the cantilever is an integrally defined portion of the base unit which is seamlessly formed together with the base unit.

8. A fluorescence detection device comprising:
a light source that emits excitation light in a first direction;
a base unit to which the light source is attached;
an opening that is defined in a side of the base unit, the side of the base unit extending in the first direction;
a cantilever that is cantilevered to the base unit to extend from an inner edge of the opening toward a center side of the opening;
an optical path conversion unit that is fixed to a free end of the cantilever, converts a traveling direction of the excitation light emitted from the light source into a second direction different from the first direction, and irradiates a measurement object with the excitation light turned in the second direction; and
a photodetection element that is disposed on a side of the opening opposite to the measurement object and detects fluorescence passing through the opening in fluorescence emitted from the measurement object irradiated with the excitation light; wherein
a fixed end of the cantilever is fixed on a side of the optical path conversion unit opposite to the light source and is fixed to the inner edge of the opening, and the cantilever extends in the first direction from the free end to which the optical path conversion unit is fixed toward the fixed end.

9. The fluorescence detection device according to claim 8,
wherein the optical path conversion unit has an adhesion surface in which an adhesive material is applied to a face provided on a side opposite to an incident side of the excitation light from the light source and facing in the first direction, and
wherein the optical path conversion unit is fixed to the cantilever by adhering the adhesion surface of the optical path conversion unit to the cantilever with the adhesive material.

10. The fluorescence detection device according to claim 9,
wherein the cantilever has an installation surface on which the optical path conversion unit is installed,
wherein the optical path conversion unit has a contact surface in planar contact with the installation surface of the cantilever, and the adhesion surface standing up relative to the installation surface of the cantilever, and
wherein, in a state in which the installation surface of the cantilever is in planar contact with the contact surface of the optical path conversion unit, a part of the cantilever is adhered to the adhesion surface of the optical path conversion unit with the adhesive material so that the installation surface of the cantilever is not adhered to the contact surface of the optical path conversion unit.

11. The fluorescence detection device according to claim 10,
wherein the cantilever has a wall portion with a shape protruding from the installation surface,
wherein the wall portion of the cantilever has a wall surface facing the adhesion surface of the optical path conversion unit with a gap therebetween, and
wherein the wall surface of the wall portion of the cantilever and the adhesion surface of the optical path conversion unit are adhered with the adhesive material being filled therebetween.

12. The fluorescence detection device according to claim 10,
wherein the optical path conversion unit is a light reflection member that has a triangular cross-sectional shape and converts an optical path through reflection, and
wherein the light reflection member having the triangular cross-sectional shape has the contact surface in planar contact with the installation surface of the cantilever, a reflection surface inclined with respect to an incident direction of the excitation light incident from the light source, and the adhesion surface standing up relative to the installation surface of the cantilever.

* * * * *